United States Patent [19]

Goldstein et al.

[11] Patent Number: 5,140,010

[45] Date of Patent: Aug. 18, 1992

[54] STABILIZED AQUEOUS FORMULATIONS OF THYMOPENTIN

[75] Inventors: Gideon Goldstein, Short Hills; Tapan Audhya, Bridgewater, both of N.J.

[73] Assignee: Immunobiology Research Institute, Annandale, N.J.

[21] Appl. No.: 665,532

[22] Filed: Mar. 6, 1991

Related U.S. Application Data

[63] Continuation-in-part of Ser. No. 413,841, Sep. 28, 1989, abandoned.

[51] Int. Cl.5 .................... A61K 37/02; C07K 7/00
[52] U.S. Cl. ........................ 514/17; 530/330; 530/301; 530/345
[58] Field of Search ............... 514/17; 530/330, 301, 530/345

[56] References Cited

U.S. PATENT DOCUMENTS

| | | | |
|---|---|---|---|
| 4,190,646 | 2/1980 | Goldstein et al. | 424/177 |
| 4,812,557 | 3/1989 | Yasushi et al. | 530/351 |

Primary Examiner—Merrell C. Cashion, Jr.
Assistant Examiner—B. Celsa
Attorney, Agent, or Firm—Howson and Howson

[57] ABSTRACT

The present invention provides a method for preparing aqueous formulations of thymopentin, which method permits the peptide to retain its biological activity during storage at room temperature.

8 Claims, 3 Drawing Sheets

STABILIZED AQUEOUS FORMULATIONS OF THYMOPENTIN

CROSS-REFERENCE TO RELATED APPLICATIONS

This application is a continuation-in-part of copending application Ser. No. 07/413,841, filed Sep. 28, 1989.

The present invention relates to stable formulations for preparations of low dosage peptides for therapeutic administration. More particularly, the invention relates to a formulation for stabilizing thymopentin in a low concentration.

BACKGROUND OF THE INVENTION

Many peptides, particularly peptides from about three to about 20 amino acids in length, are unstable in low concentrations in aqueous formulation and tend to lose biological activity, although retaining chemical stability and structure. There also exist a number of larger peptides or polypeptides which experience a similar loss of activity upon the use of low dose aqueous concentrations, e.g., encephalin, tuftsin, interleukin 2, and the brain neuropeptide, Substance P. At present the only known way to preserve the biological activity of such peptides or proteins in aqueous formulations appropriate for injectable clinical dosages is storage in high concentrations. Generally, high concentrations for storage greater than 50 mg/mL require strict refrigeration conditions, e.g., between 2° to 8° C., or approximately 4° C. Smaller concentrations, e.g., less than 10 mg/mL are frequently unstable even under strict refrigeration conditions.

One example of a peptide which experiences such biological activity loss at low concentrations in aqueous formulations is thymopentin, a pentapeptide of proven pharmacological use and significance. See, U.S. Pat. No. 4,190,646 and Goldstein, G. Nature (London) 247: 11-14 (1974); Basch, R.S. and Goldstein, G., *Proc. Natl. Acad. Sci. U.S.A.*, 71: 1474-1478 (1974); Scheid, M. P. et al, *J. Exp. Med.*, 147: 1727-1743 (1978); Scheid, M. P. et al, *Science*, 190: 1211-1213 (1975); Ranges, G. E. et al, *J. Exp. Med.*, 156: 1057-1064 (1982); T. Audhya et al., *Biochem*, 20: 6195-6200 (1981); Venkatasubramanian, K. et al, *Proc. Natl. Acad. Sci. U.S.A.*, 83: 3171-3174 (1986); Malaise M. G. et al, in "Immunoregulatory UCLA Symposium on Molecular and Cellular Biology", eds. Goldstein, G., et al (Liss, New York) (1986); Sunshine, G. H. et al, *J. Immunol.*, 120: 1594-1599 (1978) and E. Rentz et al, *Arch. Geschwulstforsch*, 54(2): 113-118 (1948). See also U.S. Pat. Nos. 4,261,886; 4,361,673; 4,420,424; and 4,629,723. These references and patents are incorporated by reference herein for their disclosure of thymopentin and methods for its preparation.

In experiments with thymopentin, it was observed that the optimal doses of thymopentin in an injectable aqueous formulation for immunostimulation in laboratory animals was about 1 μg/kg of body weight. For laboratory use, these dosages were prepared immediately prior to use. Subsequent human clinical research indicated that much larger doses, approximately 1 mg/kg body weight or greater, were required to produce a clinical pharmacological result in the patient. Preparations of clinical quantities of thymopentin at a dosage of less than 10 mg/mL in aqueous formulations were frequently found to be biologically inactive, thus accounting for a lack of efficacy of these lower concentration formulations in clinical studies.

Such activity loss in a peptide for pharmaceutical use may effect the therapeutic treatment of a patient requiring a particular pharmacologically active peptide. A loss of activity in the dosage unit will result in too little active peptide being delivered to the patient in the normal dosage unit. Thus, the appropriately effective dose of the peptide will not be given to the patient. If the activity loss is less than complete, such a variable loss will render it impossible for a practical pharmaceutical dosage to be accurately determined. Simply raising the dosage level of the peptide to compensate for this loss is not practical because the degree of loss would be unknown and excess dosages of most pharmaceuticals carry an increased risk of serious side effects. Such inefficient methods to compensate for activity loss of the peptide will also increase the cost of the pharmaceutical in question.

Additionally refrigeration at between approximately 2°-8° C. is required to maintain the biological activity of certain peptides and polypeptides, including thymopentin. For example, concentrations of thymopentin of 50 mg/mL require refrigeration to retain activity for up to and after two years, the conventional industry standard for stable pharmaceutical preparations. Lower concentrations often do not retain activity even with refrigeration. This need to refrigerate these peptides in pharmaceutical dosages severely hampers the manufacture, storage, transport and use of such peptides. For example, lack of refrigeration or fluctuation in refrigeration temperature during transportation of such peptides for therapeutic or other uses or during storage of such peptides, e.g., in countries where the appropriate clinical and pharmaceutical facilities are not available, may prevent the effective use of such peptides, even in higher concentrations.

Therefore a need exists in the art for methods of preparing an aqueous formulation of thymopentin in a manner which will retain the biological activity of clinical quantities thereof.

SUMMARY OF THE INVENTION

As one aspect, the present invention provides a method for preparing biologically active aqueous formulations of thymopentin which are stable at room temperature.

As another aspect of the present invention is provided a method for preparing biologically active aqueous formulations of low dosages of thymopentin which retain their biological activity.

As still a further aspect, the invention provides a stable aqueous preparation of thymopentin produced by the methods of the invention.

Other aspects and advantages of the present invention are described further in the following detailed description of the present invention.

DETAILED DESCRIPTION OF THE INVENTION

Figure 1:
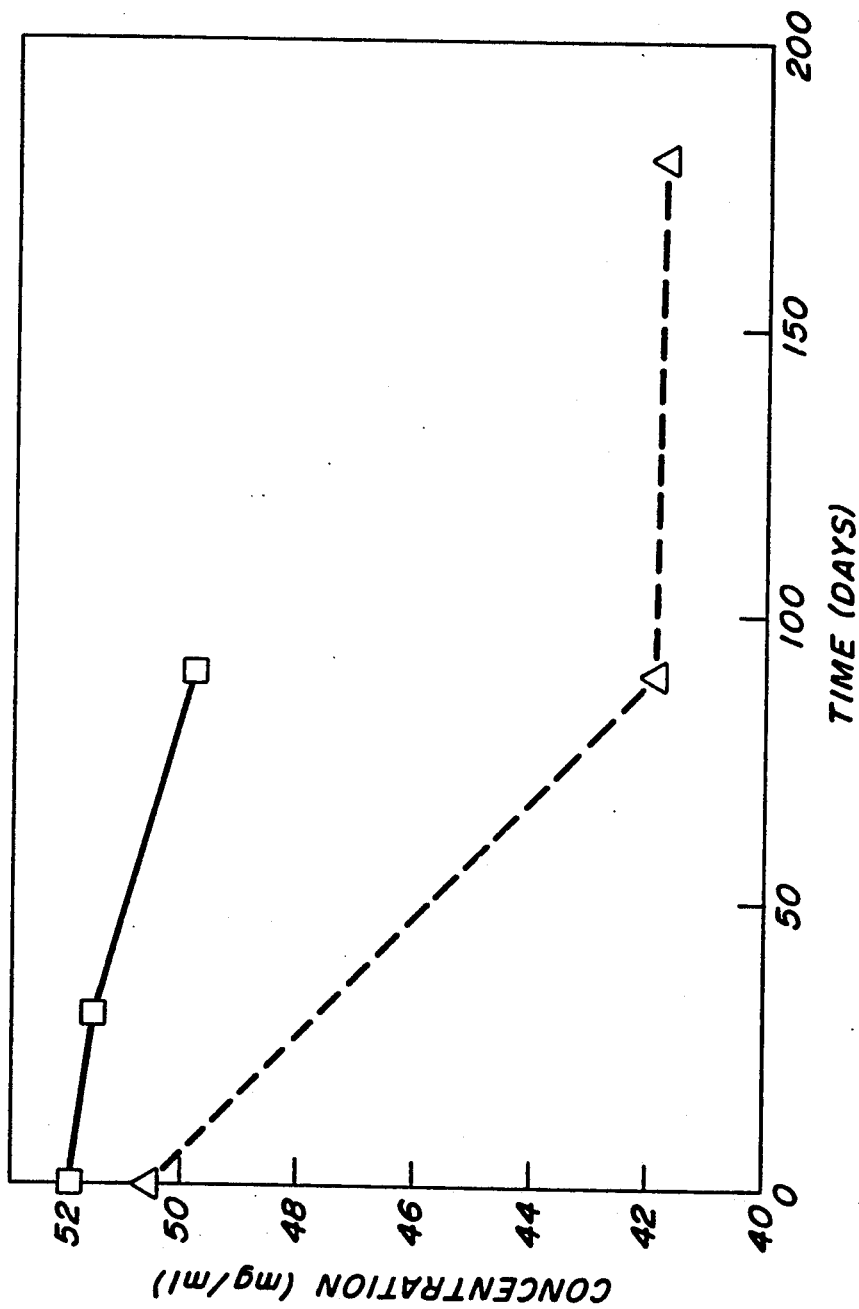
FIG. 1 is a graphical report of the stability of a thymopentin formulation according to this invention, compared with a conventional thymopentin formulation containing a standard preservative.

The present invention provides a method for stabilizing aqueous preparations of thymopentin. The method imparts stability to dosage concentrations of less than 10 mg/mL of peptides which normally demonstrate a loss in biological activity even under strict refrigeration conditions. Moreover the method has proven to be useful in increasing the stability over time of large concentrations of greater than 10 mg/mL of thymopentin in aqueous formulations, without requiring refrigeration thereof.

Prior art formulations of thymopentin experience biological activity loss upon storage or require refrigeration to retain biological activity.

According to the method of the present invention, thymopentin is prepared in a conventional pharmaceutically acceptable buffer. Because the buffer is for use in preparing a therapeutic product, desirably for use in humans, it must be non-toxic and capable of safe use in humans. Although a number of buffers which meet these qualifications may be selected by one of skill in the art, a preferred buffer according to this invention is citrate buffer. Other buffers which may be employed in this method include Hepes buffer, succinate buffer, histidine buffer, or maleate buffer.

Additionally, according to the present invention, the buffered thymopentin is desirably prepared at an appropriately controlled pH. For peptides like thymopentin for human administration, the pH is desirably in the range of from about 6.8 to about 7.4. The selection of an appropriate pH for the aqueous solution is within the skill of the art. The pH may be adjusted with appropriate acids and bases, which are physiologically safe for humans. For example, an appropriate base for such pH adjustments is sodium hydroxide. An acid such as hydrochloric acid may also be employed for pH adjustment during this method.

According to the invention, a solution is made of the thymopentin, in the selected buffer. Desirably the solution includes a concentration of between 1 to 100 mg of peptide per ml of a suitable buffer.

To the peptide solution is added a sufficient amount of glycine to stabilize the solution. Although this invention is not bound by theory, it is presently believed that the charges on the glycine molecule enhances the stability of the aqueous formulations of the thymopentin. It has been determined that other amino acids, i.e. arginine, lysine, glutamic acid, aspartic acid, histidine, tryptophan, tyrosine, alanine, proline, glutamine and aspartic acid, do not exert the stabilizing effect upon thymopentin which is achieved by the formulation of the present invention.

The glycine is added to the dilute solution of the peptide in a concentration of between 0.1 to 5% by weight. A preferred range is between 1 to 3% by weight. Presently the most preferred concentration of the amino acid in the thymopentin solution is 2% by weight.

The resulting aqueous formulation of the thymopentin is stable upon storage at ambient, or room temperature, approximately 23° C. Refrigeration is not required to maintain the biological activity of an aqueous peptide formulation prepared by the present method. For example, stabilization studies on formulations of thymopentin at concentrations of 50 mg/mL prepared according to this invention have shown that these formulations remain stable for greater than 90 days at 37° C. or at room temperature. Based on pharmaceutically acceptable standards of assay, it is anticipated that if the preparation was stable at 37° C. for 3 months, such formulations will be stable for two years at room temperature, 23° C.

The stabilization process of the present invention is appropriate for use in preparing dosage forms of thymopentin.

The following examples illustrate the method of preparing a stable aqueous formulation of thymopentin. These examples are illustrative only and do not limit the scope of the present invention.

EXAMPLE 1

To prepare a thymopentin formulation according to the present invention, the following ingredients are combined in a batch size of 20 liters: 1000.0 g (50.0 mg/mL) thymopentin adjusted for peptide content; 400.0 g (20.0 mg/mL, 2%) glycine (USP); 176.0 g (8.8 mg/mL) sodium citrate ($2H_2O$, USP); and approximately 15 liters of water for injection (USP or Ph. Eur.).

The process for preparing the formulation using the above ingredients is as follows. Approximately 15 liters of water for injection is introduced into a suitable stainless steel or glass vessel. The 400 g of glycine is added and stirred until dissolved. The 176.0 g sodium citrate ($2H_2O$) is then added and the resulting mixture stirred until the solution is clear. The appropriate quantity of thymopentin, approximately 1.163 grams, adjusted for peptide content is added, while slow stirring is continued to prevent foaming until all thymopentin is dissolved and the solution is clear.

The pH of the resulting solution is checked and adjusted to pH 7.0-7.2 utilizing 1N NaOH. If necessary, the pH may be further adjusted with 1N HCl.

Additional water for injection is added to make a volume of 20 liters. The mixture is stirred until completely mixed The solution is pre-filtered utilizing a Millipore AP 15 molecular sieve (or equivalent filter which has been soaked in water for injection) to remove any bacterial contaminants, dust or other insoluble materials from the solution. Thereafter the pre-filtered mixture is filtered again through a sterile Durapore 0.22 micron filter.

As a control, a preparation of thymopentin is made identically according to the procedure described above, except that no glycine is added to the solution.

EXAMPLE 2

Figure 2:
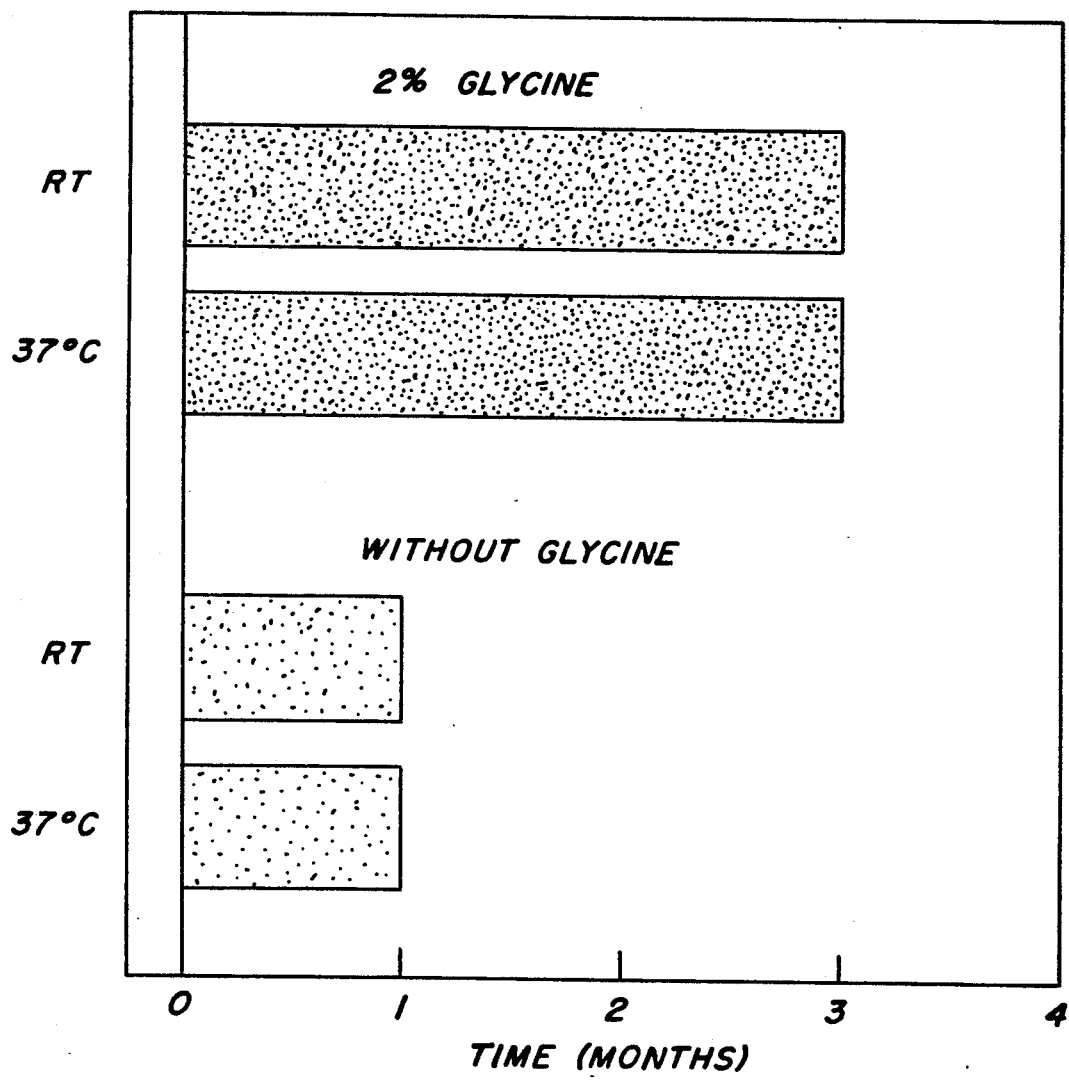
FIG. 2 is a bar graph of results of a stability test of thymopentin formulations with and without the presence of amino acid under varying temperature conditions of storage.
Figure 3:
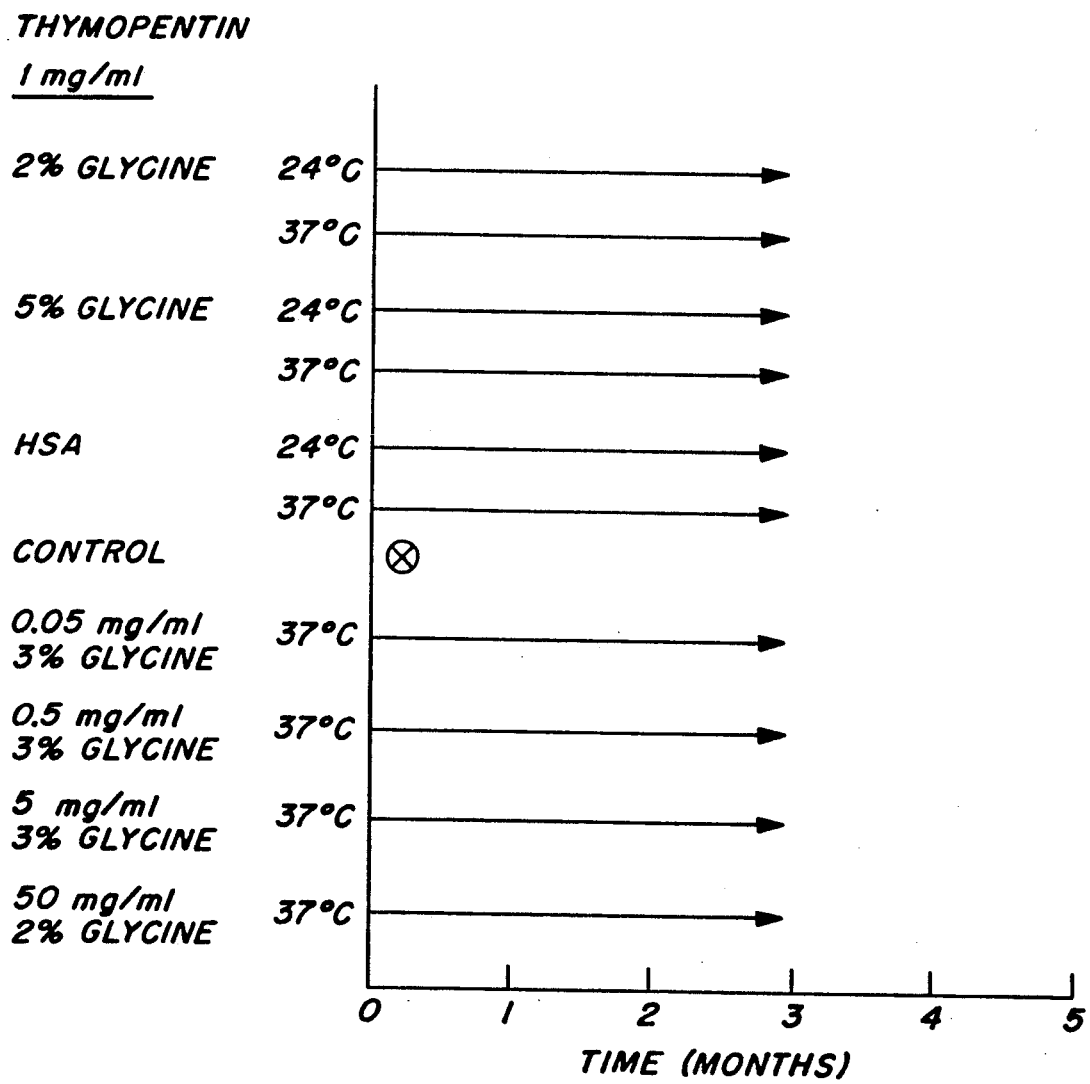
FIG. 3 is a graph of a study of various concentrations of thymopentin in formulations of this invention, compared with other formulations, under elevated temperatures of storage.

To demonstrate the stability of the compositions of this invention the thymopentin formulations of Example 1 and other formulations are stored in ampules containing 1.3 mL/ampule at approximately 24° C. and/or 37° C. for approximately 3 months. FIGS. 1 through 3 demonstrate the results of these storage times and conditions on the thymopentin compositions.

Periodically during and after storage, the formulations are assayed for biological activity according to the cyclic GMP assay. This assay is known to one of skill in the art and are disclosed in the U.S. patents and other references on thymopentin cited above. The resulting formulations made according to this invention contain stable thymopentin, which demonstrates full biological activity in this conventional thymopentin assay.

The cGMP assay measures the ability of a peptide formulation of this invention to bind to the cell membrane receptor of the intact CEM cell and selectively stimulate production of cyclic GMP. Briefly described, the CEM cell line was obtained from the American Type Culture Collection of Rockville, Md. CEM cells were freshly seeded and grown for 4 days with harvesting as described in T. Audhya et al, *Arch. Biochem Biophys.*, 234: 167–177 (1984). The cells were washed 3 times in PBS and resuspended in RPMI 1640 at a concentration of $1.0 \times 10^7$ cells/mL and were allowed to equilibrate at 37° C. for 30 minutes before the addition of the test peptide formulations (25 ul) and control peptide formulations. The incubation was allowed to proceed in a shaking water bath for 4–5 minutes and was then terminated by addition of 1 mL ice-cold 10% trichloroacetic acid (TCA).

The cells in TCA were homogenized and sonicated to release cyclic nucleotide. The suspension was centrifuged at $3000 \times$ g for 20 minutes at 4° C. The resulting precipitate was dissolved in 0.1N NaOH to determine the protein content. TCA was removed from the supernatant fraction by extracting 4 times with 5 mL of water-saturated diethyl ether. After the final extraction, the remaining traces of ether were removed by heating for 10 minutes in a 50° C. water bath. After lyophilization the sample was reconstituted in 50 mM acetate buffer (pH 6.2) for radioimmunoassay of cyclic GMP.

A threshold activity was determined for each peptide formulation tested. This is defined as the lowest concentration of the test formulation which induced an intracellular level of cyclic GMP greater than two standard deviations above the control. The controls had intracellular cyclic GMP values of less than 0.5 picomoles/mL (mean±standard deviation). Test results were considered positive if the level of cyclic GMP was greater than 2 times (2 standard deviations) that determined for the parallel negative control.

FIGS. 1–3 demonstrate the efficacy of the method of the present invention on thymopentin. In FIG. 1, the relative stability of the control solution of thymopentin containing methyl and propyl parabens and no amino acid was compared with the glycine, preservative-free formulation described in Example 1 in storage at 37° C. over time. An initial concentration of 52 mg/mL of thymopentin made according to the present invention was compared with a standard 50.7 mg/mL dosage of thymopentin. In the 90 day study, the formulation of the present invention displayed a decrease in biological activity from 52 mg/mL to approximately 50 mg/mL. In contrast the standard formulations decreased in biological activity from an effective dosage of 50.7 mg/mL to an effective dosage of 42 mg/mL.

FIG. 2 reveals another comparative study of the biological activity of thymopentin solution, in a concentration of 1 mg/mL, made according to Example 1 having 2% glycine present in solution and compared with a control solution of thymopentin, having no amino acid therein. The stability studies were conducted over three months at both room temperature, e.g., 23° C. and at an elevated temperature of 37° C. The thymopentin solution of the present invention showed stability up to three months and beyond at both temperatures of storage. The control without amino acid was inactive at all times under these temperatures.

FIG. 3 is a graph of a bioassay study performed on the thymopentin solution made according to the present invention. Three solutions of thymopentin were made at concentration of 1 mg/mL with (a) 2% glycine, (b) 5% glycine, (c) human serum albumen, and (d) no additive. These solutions were stored at two temperatures, 24° C. and 37° C. for up to three months. The solutions were assayed by the cGMP assay periodically during the storage times. All of these solutions but the control demonstrated stability up to three months at both temperatures of storage. The thymopentin solution without the amino acid or human serum albumen did not retain biological activity in the cGMP assay at any time under the temperatures of this test. Human serum albumen also enhanced the stability of the thymopentin solutions, but is not a preferred stabilizer in a therapeutic compound due to the dangers of viral transmission in serum.

The lower graph of FIG. 3 demonstrates storage of thymopentin solutions made according to the present invention at varying concentrations of thymopentin and glycine, but under three month and 37° C. storage conditions: (a) 0.05 mg/mL of thymopentin with 3% glycine; (b) 0.5 mg/mL thymopentin with 3% glycine, (c) 5 mg/mL thymopentin with 3% glycine, and (d) 50 mg/mL thymopentin with 2% glycine. All of these compositions made according to the present invention remained stable, as evidenced by activity in the cGMP bioassay, throughout the three month storage times.

Numerous modifications and variations of the present invention are included in the above-identified specification and are expected to be obvious to one of skill in the art. For example, although thymopentin was the peptide tested and reported in the Examples above, it is expected that other peptides may be treated by this method and also retain activity under harsh conditions of storage, e.g., elevated temperatures. Such modifications and alterations to the compositions and processes of the present invention are believed to be encompassed in the scope of the claims appended hereto.

What is claimed is:

1. A method for producing an aqueous formulation of the peptide thymopentin consisting essentially of preparing a solution of said peptide in a physiologically acceptable aqueous buffer with between 0.1 to 5% by weight of the amino acid glycine, said thymopentin in the aqueous formation being capable of retaining its biological activity under temperature conditions of up to 37° C.

2. The method according to claim 1 wherein said amino acid concentration is 2% by weight.

3. The method according to claim 1 wherein said buffer is citrate buffer.

4. The method according to claim 1 wherein said aqueous formulation has a pH of between 6.2 and 7.4.

5. An aqueous formulation of the peptide thymopentin prepared by the method of claim 1.

6. An aqueous thymopentin formulation capable of retaining its biological activity under temperature conditions of up to 37° C. comprising between 0.1 to 5% by weight glycine and thymopentin in a physiologically acceptable aqueous buffer.

7. The formulation according to claim 6 further comprising a concentration of between 1 to 100 mg of thymopentin per ml of buffer.

8. The formulation according to claim 6 wherein the glycine is 1–3% by weight.

* * * * *